(12) United States Patent
Schomann

(10) Patent No.: US 7,029,279 B2
(45) Date of Patent: Apr. 18, 2006

(54) PROSTHODONTIA SYSTEM

(76) Inventor: Mark Schomann, 101 Quarfelt Rd., Clinton Corners, NY (US) 12514

( * ) Notice: Subject to any disclaimer, the term of this patent is extended or adjusted under 35 U.S.C. 154(b) by 244 days.

(21) Appl. No.: 10/265,490

(22) Filed: Oct. 7, 2002

(65) Prior Publication Data

US 2004/0067465 A1    Apr. 8, 2004

(51) Int. Cl.
*A61C 19/10* (2006.01)
(52) U.S. Cl. .................................. 433/223; 433/203.1
(58) Field of Classification Search ................ 433/26, 433/202.1, 223, 203.1, 215
See application file for complete search history.

(56) References Cited

U.S. PATENT DOCUMENTS

| | | | |
|---|---|---|---|
| 4,182,312 A | 1/1980 | Mushabac |
| 4,478,580 A | 10/1984 | Barrut |
| 4,575,805 A | 3/1986 | Moermann et al. |
| 4,654,794 A | 3/1987 | O'Brien |
| 4,935,635 A | 6/1990 | O'Harra |
| 4,937,928 A | 7/1990 | van der Zel |
| 5,224,049 A | 6/1993 | Mushabac |
| 5,237,998 A | 8/1993 | Duret et al. |
| 5,273,429 A | 12/1993 | Rekow et al. |
| 5,284,442 A | 2/1994 | Peterson |
| 5,320,462 A | 6/1994 | Johansson et al. |
| 5,378,154 A | 1/1995 | Van Der Zel |
| 5,555,884 A | 9/1996 | Nonomura |
| 5,823,778 A | 10/1998 | Schmitt et al. |
| 5,851,115 A | 12/1998 | Carlsson et al. |
| 5,857,853 A | 1/1999 | van Nifterick et al. |
| 5,902,441 A | 5/1999 | Bredt et al. |
| 5,989,029 A | 11/1999 | Osorio et al. |
| 5,993,214 A | 11/1999 | Persson |
| 6,007,318 A | 12/1999 | Russell et al. |
| 6,068,482 A | 5/2000 | Snow |
| 6,099,314 A | 8/2000 | Kopelman et al. |
| 6,217,334 B1 | 4/2001 | Hultgren |
| 6,261,098 B1 | 7/2001 | Persson |
| 6,287,121 B1 | 9/2001 | Guiot et al. |
| 6,322,728 B1 | 11/2001 | Brodkin et al. |

(Continued)

FOREIGN PATENT DOCUMENTS

DE          3810455 A1    10/1989

OTHER PUBLICATIONS

Computer Vision Technique, By Denis Laurendeau, IEEE Transactions on Medical Imagaing, vol. 10, No. 3, Sep. 1991.

*Primary Examiner*—Melba N. Bumgarner
(74) *Attorney, Agent, or Firm*—Seth Natter; Natter & Natter

(57) ABSTRACT

A processor implemented prosthodontia system employs digital imaging of a restoration site and surrounding areas of an oral cavity and digital sampling of colorimetric values of tooth surfaces. The processor selects digital image data representative of a tooth surface configuration corresponding to the tooth number of the tooth to be restored and generates a three dimensional image of the restoration, with colorimetric values. Data comprising the shape and colorimetric values of the restoration is transmitted to a fabrication station for processor controlled fabrication through implementation of, for example, a three dimensional jet printing system employing particulate porcelain, polymeric dental composite, etc., and a binder, solvent or reactant and which builds a preform in successive layers of incremental cross sectional heighths. The shaped and colored preform is then hardened to produce a restoration having the specified size, shape and colorimetric values.

6 Claims, 2 Drawing Sheets

U.S. PATENT DOCUMENTS 6,328,567 B1 * 12/2001 Morris et al. ............... 433/215
6,375,874 B1    4/2002  Russell et al.
6,416,850 B1    7/2002  Bredt et al.
6,808,659 B1 * 10/2004 Schulman et al. ............ 264/16
2003/0207228 A1 * 11/2003 Lehmann et al. ............. 433/26
2003/0207235 A1 * 11/2003 der Zel ....................... 433/223

* cited by examiner

PROSTHODONTIA SYSTEM

BACKGROUND OF THE INVENTION

1. Field of the Invention

This invention relates generally to the practice of prosthodontia and more particularly to a processor implemented system for design and fabrication of dental restorations.

2. Antecedents of the Invention

Prior methods of fabrication of dental restoratives, prosthesis or restorations such as crowns, bridges and the like, were taxing, time consuming procedures entailing both a dental practitioner as well as a laboratory technician. The dental practitioner generally utilized a dental impression material to form impressions, with the impressions then being employed to cast rigid models, which were then utilized by the dental laboratory technician to fabricate the restoration.

The precise dimensions, shape and coloration of the restoration were subjective parameters, dependent upon the expertise and experience of both the dental practitioner and the dental laboratory technician. Emplacement of the restoration in the oral cavity was also a time consuming practice which involved grinding surfaces of the restoration for occlusal and interproximal fit. Often, a restoration which fit well would be unsatisfactory in hue, chroma, luminous intensity or opacity, due to the subjective nature of color matching and the effects of artificial light at the practitioner's office which resulted in imperfect color matching when the restoration was viewed under different lighting conditions.

The procedure was expensive, labor intensive, time consuming and an inconvenience to the patient, due to the requirement for numerous visits to the dental practitioner.

With the advent of computer aided design systems, attempts were made to utilize processors for determining the shape of a restoration, based upon physical measurements or optical scans of the restoration site in combination with the utilization of processor controlled fabrication, e.g. cutting or milling of the restoration itself. Examples of typical proposed CAD-CAM systems were disclosed in the patents to CARLSSON, U.S. Pat. No. 5,851,115, NONOMURA, U.S. Pat. No. 5,555,884, JOHANNSON, U.S. Pat. No. 5,320,462, VAN ZER ZEL, U.S. Pat. No. 4,937,928, O'HARRA, U.S. Pat. No. 4,935,635 and MOERMANN, U.S. Pat. No. 4,575,805.

Further attempts were made in connection with computer-aided design of dental restorations which employed scanning a model of the restoration site and adjacent areas, as disclosed in the patents to GUIOT, U.S. Pat. No. 6,287,121, HULTGREN, U.S. Pat. No. 6,217,334 and SCHMITT, U.S. Pat. No. 5,823,778.

None of these prior systems resulted in a dental restoration having computer generated colorimetric values. Since these systems generally fabricated the restoration by milling or cutting from a block of material, the final colorimetric appearance of the restoration involved the manual application of a pigmented coating or the preselection of a starting mass or block of restoration material which was uniformly colored and selected, utilizing subjective color chart matching.

SUMMARY OF THE INVENTION

A prosthodontia system employs a noncontact scanner to generate digitized three-dimensional representations (images) of a patient's oral cavity including the site of a restoration or prosthesis as well as' adjacent and occlusive tooth surfaces. When the restoration comprises a crown, scanning may occur prior to the preparation of a tooth remnant or abutment, followed by a scanning after the remnant or abutment surface has been shaped to accept a restoration.

In accordance with the invention, digital sampling of colorimetric values of the surfaces of the tooth remnant as well as adjacent tooth surfaces are also obtained.

The processor then utilizes the scanned digital image data, the colorimetric value data and digital image data of a preferred tooth configuration corresponding to the tooth number and tooth dimensions of the tooth to be restored. As a function of such data, the processor generates a digital image of the restoration in both its three dimensional shape and surface colorimetric values.

The data comprising the digital image and coloration of the restoration is received at a fabrication station. The restoration may be fabricated employing a processor controlled three-dimensional jet printing system, which builds a restoration preform having the appropriate colorimetric values in successive layers of incremental heights. The preform is then hardened by curing or sintering, for example, and thereafter polished.

The entire prosthodontia system may be situate in a dental practitioner's office such that the restoration may be designed, fabricated and emplaced in a single patient visit. Alternatively, the fabrication station is at a remote site which fabricates restorations for a plurality of dental practitioners.

From the foregoing compendium, it will be appreciated that it is an aspect of the present invention to provide a prosthodontia system of the general character described which is not subject to the disadvantages of the antecedents of the invention aforementioned.

A feature of the present invention is to provide a prosthodontia system of the general character described which reduces the cost of dental restorations.

A consideration of the present invention is to provide a prosthodontia system of the general character described which reduces the inconvenience to patients normally associated with obtaining dental restorations.

Another aspect of the present invention is to provide a prosthodontia system of the general character described which implements processor controlled coloration of a restoration with appropriate colorimetric values matching those of the remaining teeth in a patient's mouth.

To provide a prosthodontia system of the general character described which employs a processor controlled three-dimensional jet printing system for fabricating a dental restoration is a further feature of the present invention.

A further consideration of the present invention is to provide a prosthodontia system of the general character described wherein the design, fabrication and fitting of a dental restoration may take place at a single visit to a dental practitioner's office.

Another aspect of the present invention is to provide a prosthodontia system of the general character described which eliminates subjective determinations.

A still further consideration of the present invention is to provide a prosthodontia system of the general character described which simplifies the design, fabrication and fitting of a restoration.

A still further feature of the present invention is to provide a prosthodontia system of the general character described which increase the dental practitioner's efficiency.

Other aspects features and considerations in part will be obvious and in part will be pointed out herein after.

With these ends in view, the invention finds embodiment in the certain combinations of elements, arrangements of parts and series of step by which the aforesaid aspects, features and considerations and certain other aspects, features and considerations are attained, all with reference to the accompanying drawings and the scope of which will be more particularly pointed out and indicated in the appended claims.

BRIEF DESCRIPTION OF THE DRAWINGS

The accompanying drawings, in which is shown one of the various possible exemplary embodiments of the invention.

DESCRIPTION OF THE PREFERRED EMBODIMENTS

Figure 1:
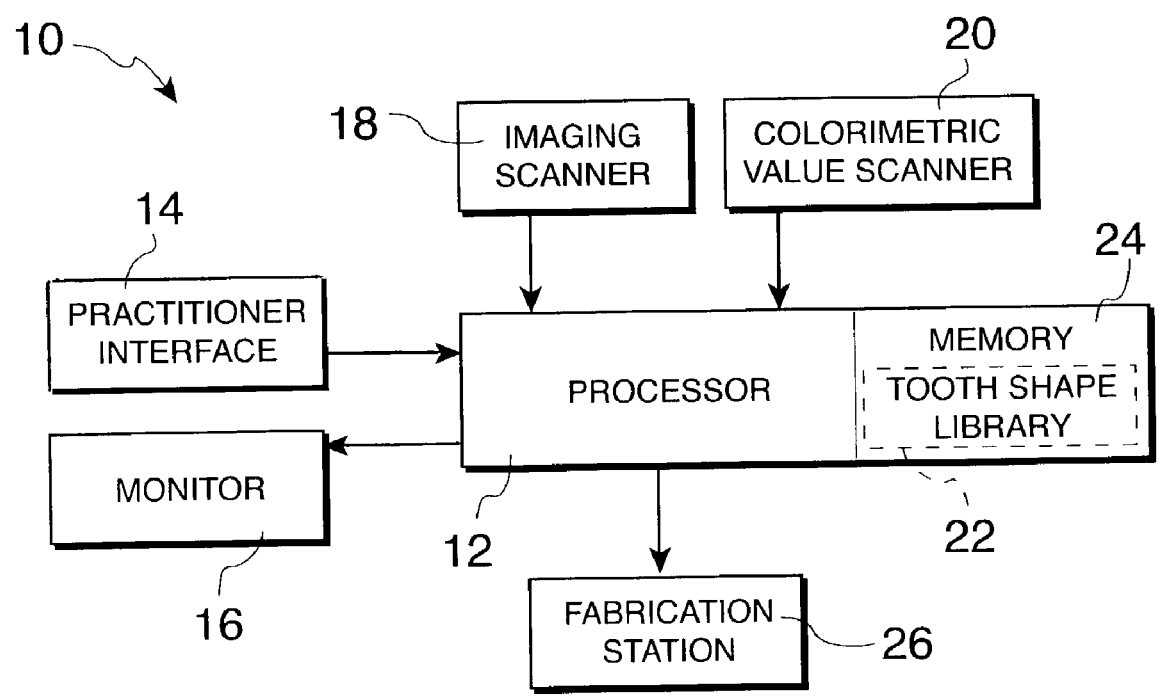
FIG. 1 is a schematized block diagram illustrating the major components of a prosthodontia system constructed in accordance with and embodying the invention and illustrating a processor in communication with an imaging scanner, a colorimetric value sampler and a fabrication station which receives data from the processor for the fabrication of a dental restoration.

The term restoration, as employed herein should be construed in the broadest sense to include a dental restorative, a prosthesis of any kind or nature, such as a crown, cap, bridge, and crown-bridge and the term remnant should be construed to include any natural tooth portion to which the restoration is attached as well as abutments, posts and the like.

Referring now in detail to the drawings, the reference numeral 10 denotes generally a prosthodontia system constructed in accordance with and embodying the invention. The system includes a processor 12 in communication with the dental practitioner through a practitioner interface 14 and a monitor 16.

The system 10 further includes an imaging scanner 18, preferably configured for noncontact digital imaging of a patient's oral cavity. Suitable scanners may include laser optical probes, laser diodes and other scanning systems referred to in the aforementioned patents to CARLSSON, JOHANNSON, VAN ZER ZEL, O'HARA and MOERMANN or an MRI scanner as disclosed in the NONOMURA patent, all of which are incorporated herein by reference. It should be appreciated that any type of scanning device which is capable of generating digital images of affected teeth, the restoration site and surrounding surfaces of the oral cavity, including contact type devices may also be employed in conjunction with the invention.

In addition to the imaging scanner 18, a colorimetric value sampler 20 is coupled to the processor. The colorimetric value sampler 20 may comprise a sampling device such as that illustrated in the patent to O'BRIEN, U.S. Pat. No. 4,654,794, incorporated herein by reference or a device currently marketed under the mark X-RIGHT SHADE VISION SYSTEM manufactured by X-Right Corporation of Grandville, Mich. and distributed by Sullivan-Schein Dental of Melville, N.Y. The X-RIGHT SHADE VISION SYSTEM comprises a calorimeter which captures and digitizes the colorimetric values of teeth in hue, chroma, and luminous intensity as well as opacity.

Also associated with the processor is a library 22 of preferred tooth configurations stored in a memory 24.

The prosthodontia system additionally includes a fabrication station 26 which may be located at the same premises or at a remote location. Pursuant to the invention, the fabrication station 26 preferably comprises a processor implemented three-dimensional jet printing system which builds a restoration preform having appropriate colorimetric values in successive layers of incremental cross sectional heighths. Processor controlled fabrication equipment suitable for implementation in the present invention are generally disclosed in the patent to BREDT et al., U.S. Pat. No. 6,416,850, RUSSELL et al., U.S. Pat. No. 6,375,874, RUSSELL et al., U.S. Pat. No. 6,007,318, BREDT et al., U.S. Pat. No. 5,902,441, which are incorporated herein by reference.

A suitable fabrication station apparatus may comprise the Z400 series printing systems available from Z Corporation of Burlington, Mass. In operation, a dental restoration is fabricated by depositing a layer of particulate restoration material, e.g. porcelain or a polymeric dental composite, and then building successive individual incremental heighths of cross sectional areas of the restoration by using an ink-jet print head to deliver a solvent, binder or reactant to the particles, causing the particles to adhere together and to the underlying incremental heighth of cross sectional area of the restoration.

Figure 2:
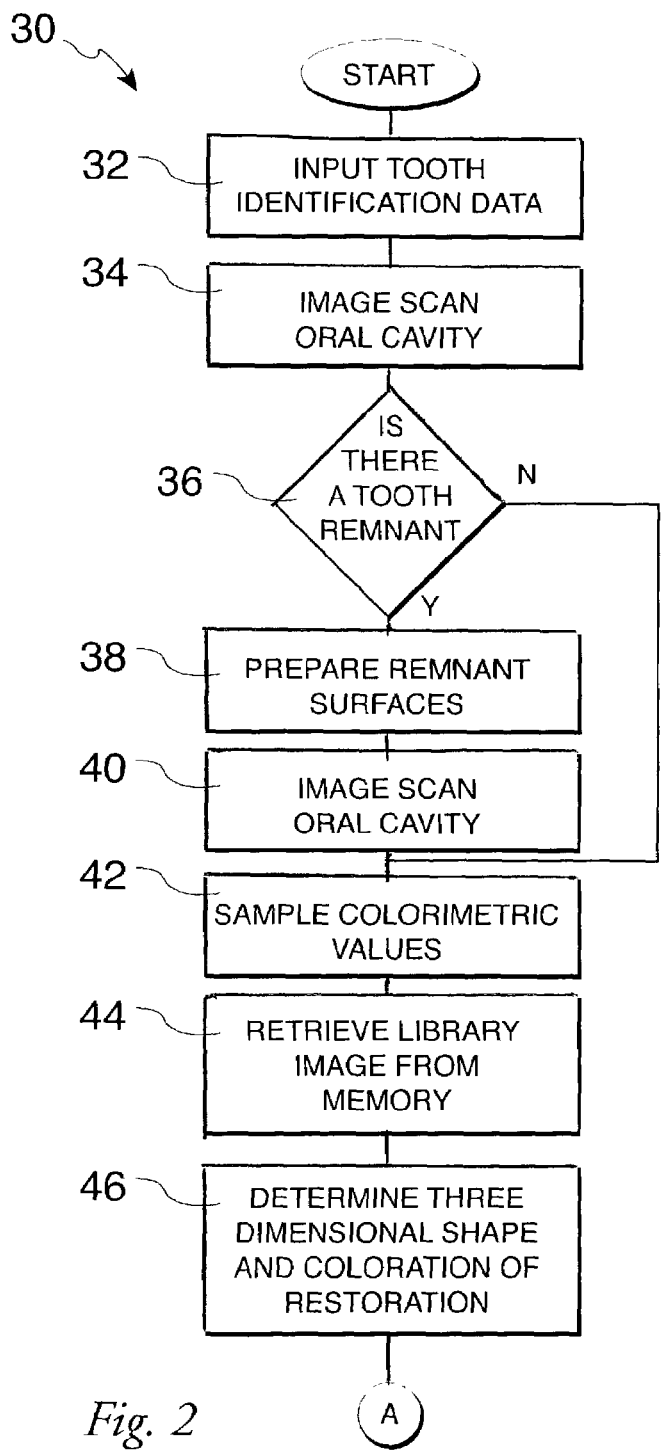
FIG. 2 is a flow chart depicting some of the steps in practicing the prosthodontia system in accordance with the invention.
Figure 3:
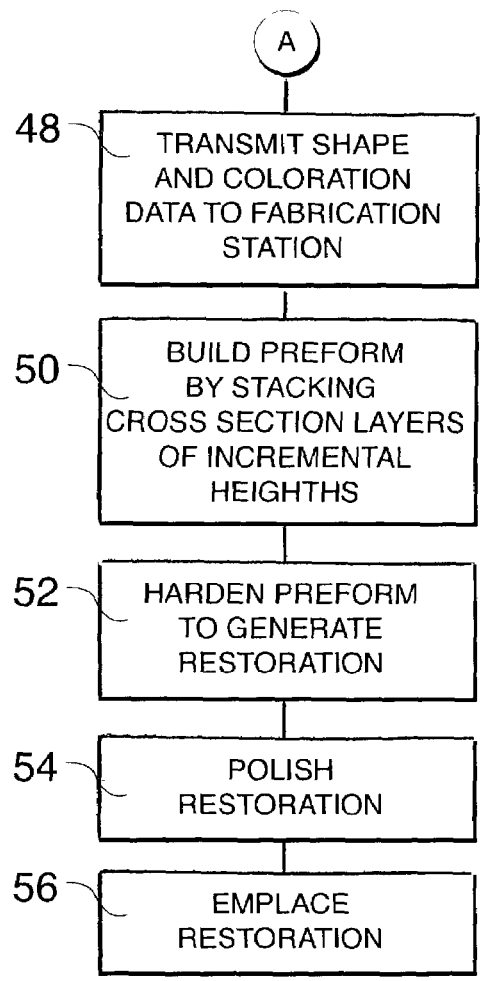
FIG. 3 is a depiction of remaining steps in practicing the prosthodontia system.

For a more complete understanding of the process for designing, fabricating and fitting a restoration pursuant to the invention, attention is directed to FIG. 2 and FIG. 3 wherein various steps, designated collectively by the numeral 30, are depicted.

Upon commencing the procedure of the invention, the dental practitioner employs the interface 14 to input into the processor tooth identification data corresponding to the tooth which is being replaced or restored, as indicated in a block 32. The practitioner utilizes, as the interface, a keyboard and/or computer mouse with the tooth identification data comprising, for example, the numerical designation of the tooth or teeth being restored and may additionally include size measurements or other designations corresponding to such tooth or teeth.

The dental practitioner thereafter employs the oral imaging scanner 18 to generate digitized three-dimensional digital images of the affected teeth, i.e. the restoration site, adjacent teeth as well as occlusal tooth surfaces as indicated in a block 34. Thereafter, an inquiry is made as to whether or not there is a tooth remnant or abutment to which a restoration is to be attached. If there is a tooth remnant, the tooth remnant surfaces or the surfaces of an abutment are prepared for receiving a restoration as indicated in a block 38. The oral cavity is thereafter digitally rescanned for three-dimensional imaging as indicated in a block 40.

Sample colorimetric values are obtained through utilization of the colorimetric value sampler 20. In the event there was no tooth remnant for surface preparation when the inquiry was made in the block 36, the next step in the prosthodontia procedure would route to a block 42, i.e. sampling for colorimetric values.

The dental practitioner utilizes the colorimetric value sampler 20 to obtain colorimetric values of the tooth remnant and adjacent tooth surfaces, as indicated in the block 42.

The digital images as well as the digitized colorimetric values are transmitted to the processor 12. The processor 12 additionally retrieves, from the memory 24, a preferred tooth configuration from the tooth shape library 22, as indicated in a block 44.

The processor then generates the three dimensional shape and coloration of the restoration as a function of the digitized three-dimensional images, the digitized preferred tooth configuration and the digitized colorimetric values, all as indicated in a block 46.

After generating the three dimensional shape and coloration of the restoration, the processor transmits the shape and coloration data to the fabrication station 26, as indicated in a block 48.

It should be noted that at the fabrication station 26, the prosthodontia procedure continues as indicated in FIG. 3 and a preform is built by stacking layers of incremental heighths of the cross sectional areas of the restoration, as indicated in a block 50. The preform is thereafter hardened, as by sintering, light curing, aging or the like, to produce a properly dimensioned hard restoration having the appropriate colorimetric values, as indicated in a block 52.

The dental practitioner may then polish the restoration, as indicated in the block 54 and proceed with emplacement of the restoration as by cementation, as indicated in a block 56.

It should be appreciated that the restoration could comprise, rather than a single unitary body, a core formed of metal, ceramic or other material and a porcelain or polymeric dental composite overlay, both of which are separately fabricated in incremental cross sectional heighths at the fabrication station 26. The overlay having the specified colorimetric values, would then be mounted over the core, either before or after the curing or sintering operations. If the composite restoration is assembled after the core and overlay have been hardened, a suitable cement would be applied for bonding.

Thus, it will be seen that there is provided a prosthodontia system which achieves the various aspects, features and considerations of the present invention and which is well suited to meet the conditions of practical usage.

Since various embodiments of the present invention might be made without departing from the spirit thereof, it is to be understood that all matter herein shown or described is to be interpreted as illustrative and not in the limiting sense.

Having thus described the invention, there is claimed as new and desired to be secured by Letters Patent:

1. A method of fabricating a restoration preform with a prosthodontia system comprising an imaging scanner for generating digital signals, corresponding to three dimensional images of a site in an oral cavity, a colorimetric value sampler for generating digital signals corresponding to colorimetric values of at least one tooth surface in the oral cavity, a processor operatively connected to the imaging scanner and to the colorimetric value sampler, a memory associated with the processor storing a tooth shape library comprising data representative of a plurality of tooth configurations, the system further including a fabrication station, the preform comprising a particulate material adhered with a binder, the method comprising the steps of:
   a) generating digital signals corresponding to three dimensional images of the site in the oral cavity with the imaging scanner,
   b) generating digital signals corresponding to colorimetric values of at least one tooth surface in the oral cavity,
   c) retrieving data representative of a preferred tooth configuration corresponding to the site,
   d) generating a signal defining the three dimensional shape and colorimetric values of a restoration as a function of the imaging scanner signals, the colorimetric value sampler signals and the retrieved preferred tooth configuration data,
   e) fabricating the restoration preform at the fabrication station by stacking a plurality of cross sectional incremental layers as a function of the signal defining the three dimensional shape and colorimetric values of the restoration.

2. A method in accordance with claim 1 wherein step e) is performed with a three-dimensional jet printing system.

3. A method in accordance with claim 2, the three dimensional jet printing system including at least one jet for depositing the binder in the configuration of a cross sectional layer of the restoration, step e) further including depositing the binder on successive layers of particulate material.

4. A method in accordance with claim 3 wherein the binder includes a coloring agent.

5. A method in accordance with claim 3 wherein the particulate material comprises porcelain.

6. A method in accordance with claim 3 wherein the binder comprises a solvent.

\* \* \* \* \*